(12) United States Patent
Bitsch-Larsen et al.

(10) Patent No.: US 11,203,564 B2
(45) Date of Patent: Dec. 21, 2021

(54) ROUTING OF PURIFIED AROMATIC CARBOXYLIC ACID FILTER RINSE FOR ENERGY OPTIMIZATION

(71) Applicant: Ineos US Chemicals Company, Naperville, IL (US)

(72) Inventors: Anders Bitsch-Larsen, Wheaton, IL (US); Tian Liang, Zhuhai (CN)

(73) Assignee: INEOS US CHEMICALS COMPANY, Warrenville, IL (US)

( * ) Notice: Subject to any disclaimer, the term of this patent is extended or adjusted under 35 U.S.C. 154(b) by 6 days.

(21) Appl. No.: 16/633,945

(22) PCT Filed: Jul. 25, 2017

(86) PCT No.: PCT/CN2017/094288
§ 371 (c)(1),
(2) Date: Jan. 24, 2020

(87) PCT Pub. No.: WO2019/019012
PCT Pub. Date: Jan. 31, 2019

(65) Prior Publication Data
US 2020/0216380 A1    Jul. 9, 2020

(51) Int. Cl.
*C07C 51/43* (2006.01)
*B01D 9/00* (2006.01)
(Continued)

(52) U.S. Cl.
CPC ............ *C07C 51/43* (2013.01); *B01D 9/0059* (2013.01); *B01D 39/083* (2013.01); *C07C 51/47* (2013.01);
(Continued)

(58) Field of Classification Search
None
See application file for complete search history.

(56) References Cited

U.S. PATENT DOCUMENTS

| 2,741,369 A | 4/1956 | Fest |
| 5,723,656 A | 3/1998 | Abrams |

(Continued)

FOREIGN PATENT DOCUMENTS

| EP | 0630673 A1 | 12/1994 |
| WO | 2016014830 A1 | 1/2016 |

OTHER PUBLICATIONS

International Search Report and Written Opinion for PCT/CN2017/094288, 6 pages, dated Dec. 29, 2017.

*Primary Examiner* — Sudhakar Katakam
*Assistant Examiner* — Jennifer C Sawyer
(74) *Attorney, Agent, or Firm* — McDonnell, Boehnen, Hulbert & Berghoff LLP

(57) ABSTRACT

A process for manufacturing a purified aromatic carboxylic acid is provided. The process comprises purifying a crude aromatic carboxylic acid in a purification zone to form a purified aromatic carboxylic acid; crystallizing a purified aromatic carboxylic acid in a crystallization zone to form a solid/liquid mixture comprising purified aromatic carboxylic acid solids; filtering the solid/liquid mixture through a filter member of a rotary pressure filter apparatus to form a filter cake comprising the purified aromatic carboxylic acid solids; removing the filter cake from the filter member; rinsing the filter member to produce a filter rinse product, wherein the filter rinse product comprises purified aromatic carboxylic acid; and directing at least a portion of the filter rinse product downstream of the purification zone for recycle to the rotary pressure filter apparatus.

14 Claims, 3 Drawing Sheets

(51) Int. Cl.
*B01D 39/08* (2006.01)
*C07C 51/47* (2006.01)
*C07C 63/26* (2006.01)

(52) U.S. Cl.
CPC ...... *B01D 2009/0086* (2013.01); *C07C 63/26* (2013.01)

(56) References Cited

U.S. PATENT DOCUMENTS

| | | |
|---|---|---|
| 6,137,001 A | 10/2000 | Broeker et al. |
| 7,807,060 B2 | 10/2010 | Schmid |
| 7,935,844 B2 | 5/2011 | Bartos |
| 7,935,845 B2 | 5/2011 | Bartos |
| 8,173,834 B2 | 5/2012 | Bartos |
| 2005/0051473 A1 | 3/2005 | Suss et al. |
| 2015/0182890 A1 | 7/2015 | Keyes et al. |
| 2015/0183705 A1 | 7/2015 | Metelski |
| 2015/0183709 A1 | 7/2015 | Bartos |
| 2018/0207558 A1* | 7/2018 | Bitsch-Larsen ...... B01D 33/067 |

\* cited by examiner

ROUTING OF PURIFIED AROMATIC CARBOXYLIC ACID FILTER RINSE FOR ENERGY OPTIMIZATION

CROSS-REFERENCE TO RELATED APPLICATIONS

The present application is a U.S. National Stage filing under 35 U.S.C. § 371 of International Patent Application no. PCT/CN2017/094288, filed Jul. 25, 2017.

TECHNICAL FIELD

The present teachings relate generally to processes for manufacturing purified aromatic carboxylic acids.

BACKGROUND

Terephthalic acid (TA) and other aromatic carboxylic acids may be used in the manufacture of polyesters (e.g., via their reaction with ethylene glycol and/or higher alkylene glycols). Polyesters in turn may be used to make fibers, films, containers, bottles, other packaging materials, molded articles, and the like.

In commercial practice, aromatic carboxylic acids have been made by liquid phase oxidation of methyl-substituted benzene and naphthalene feedstocks in an aqueous acetic acid solvent. The positions of the methyl substituents correspond to the positions of carboxyl groups in the aromatic carboxylic acid product. Air or other sources of oxygen (e.g., typically in a gaseous state) have been used as oxidants in the presence, for example, of a bromine-promoted catalyst that contains cobalt and manganese. The oxidation is exothermic and yields aromatic carboxylic acid together with by-products, including partial or intermediate oxidation products of the aromatic feedstock, and acetic acid reaction products (e.g., methanol, methyl acetate, and methyl bromide). Water is also generated as a by-product.

Pure forms of aromatic carboxylic acids are oftentimes desirable for the manufacture of polyesters to be used in important applications (e.g., fibers and bottles). Impurities in the acids (e.g., by-products generated from oxidation of aromatic feedstocks and, more generally, various carbonyl-substituted aromatic species) are thought to cause and/or correlate with color formation in polyesters made therefrom, which in turn leads to off-color in polyester converted products. Aromatic carboxylic acids having reduced levels of impurities may be made by further oxidizing crude products from liquid phase oxidation as described above at one or more progressively lower temperatures and oxygen levels. In addition, partial oxidation products may be recovered during crystallization and converted into the desired acid product.

Pure forms of terephthalic acid and other aromatic carboxylic acids having reduced amounts of impurities—for example, purified terephthalic acid (PTA)—have been made by catalytically hydrogenating less pure forms of the acids or so-called medium purity products in solution using a noble metal catalyst. In commercial practice, liquid phase oxidation of alkyl aromatic feed materials to crude aromatic carboxylic acid, and purification of the crude product, are oftentimes conducted in continuous integrated processes in which crude product from the liquid phase oxidation is used as a starting material for the purification.

In conventional processes, the effluent from the hydrogenation reactor is cooled by flash crystallization. This forces the PTA to come out of solution creating a slurry of about 30-55 percent solids by weight. The slurry is then treated by a solid/liquid separation device to remove the PTA mother liquor and deliver it to a PTA dryer. The solid/liquid separation can be performed by a pressure filter, pressure centrifuge, rotary vacuum filter, or similar device. When a pressure filter is used, one of the challenges is to remove all the PTA solids from the filter members. These solids need to be removed prior to refilling the pressure filter with new material to avoid fouling of the filter members and to ensure that pressure filter can be filled evenly such that the maximum wash and drying efficiency can be obtained. The solids are typically removed by steps of washing the filter member with a liquid, but gas can also be used. The step is commonly known as "filter rinsing." The resulting "filter rinse product" (i.e., the wash liquid containing some purified aromatic carboxylic acid solids) is typically routed back to a point upstream of the hydrogenation reactor, and thus has to be heated before entering the hydrogenation reactor, resulting in an energy penalty.

Thus, there is a need for a process for a more efficient way of recycling the filter rinse product.

SUMMARY

The scope of the present invention is defined solely by the appended claims, and is not affected to any degree by the statements within this summary.

According to one aspect of the invention, a process for manufacturing a purified aromatic carboxylic acid is provided. The process comprises purifying a crude aromatic carboxylic acid in a purification zone to form a purified aromatic carboxylic acid; crystallizing a purified aromatic carboxylic acid in a crystallization zone to form a solid/liquid mixture comprising purified aromatic carboxylic acid solids; filtering the solid/liquid mixture through a filter member of a rotary pressure filter apparatus to form a filter cake comprising the purified aromatic carboxylic acid solids; removing the filter cake from the filter member; rinsing the filter member to produce a filter rinse product, wherein the filter rinse product comprises purified aromatic carboxylic acid; and directing at least a portion of the filter rinse product downstream of the purification zone for recycle to the rotary pressure filter apparatus. The invention provides a routing of purified aromatic carboxylic acid filter rinse for energy optimization.

Other aspects of the invention will be apparent to those skilled in the art in view of the description that follows.

DETAILED DESCRIPTION

Figure 1:
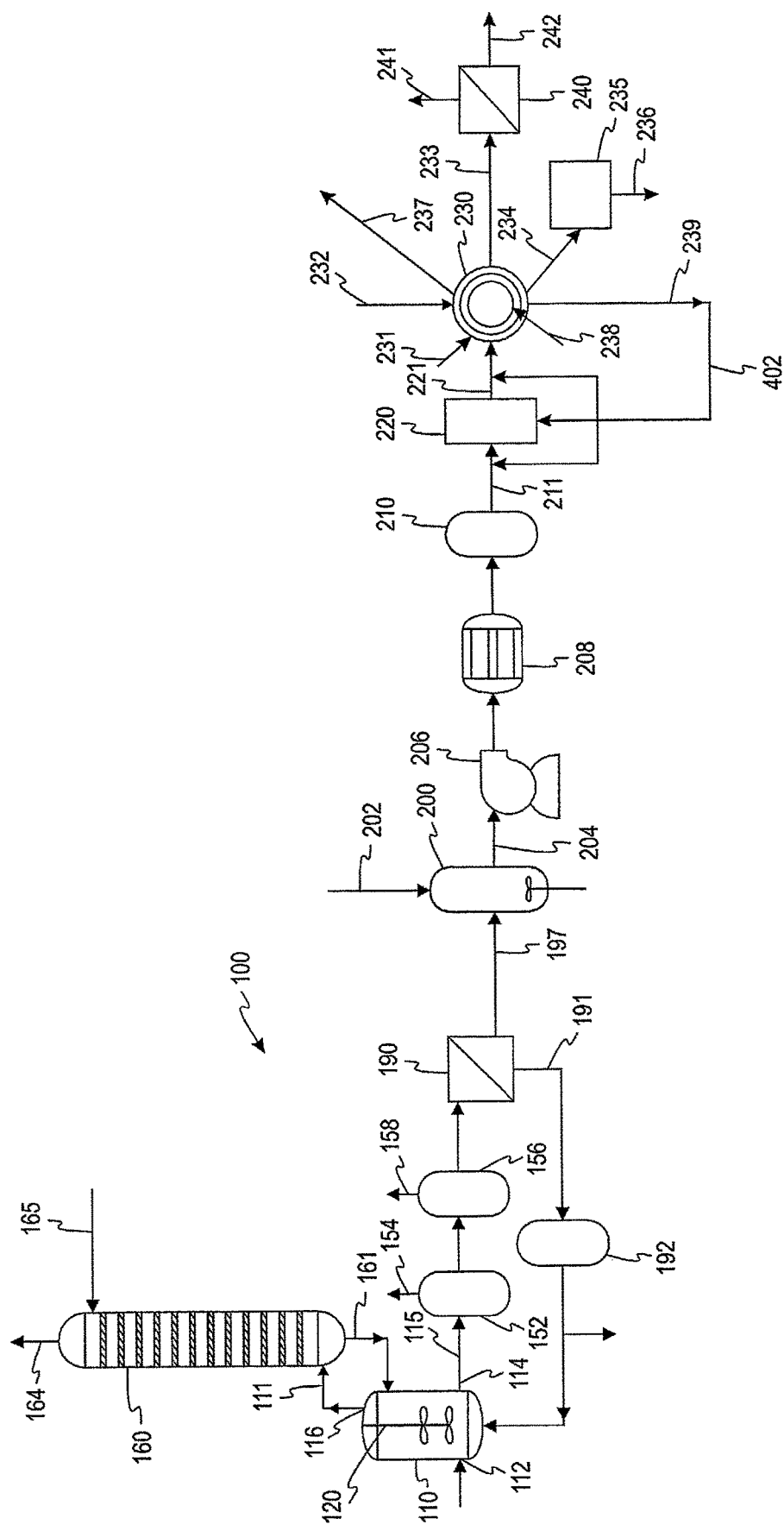
FIG. 1 shows a process flow diagram for manufacturing and recovering purified forms of aromatic carboxylic acids in accordance with one embodiment of the present teachings.

By way of general introduction, a process for manufacturing a purified aromatic carboxylic acid in accordance with the present invention comprises: purifying a crude aromatic carboxylic acid in a purification zone to form a purified aromatic carboxylic acid; crystallizing a purified aromatic carboxylic acid in a crystallization zone to form a solid/liquid mixture comprising purified aromatic carboxylic acid solids; filtering the solid/liquid mixture through a filter member of a rotary pressure filter apparatus to form a filter cake comprising the purified aromatic carboxylic acid solids; removing the filter cake from the filter member; rinsing the filter member to produce a filter rinse product, wherein the filter rinse product comprises purified aromatic carboxylic acid; and directing at least a portion of the filter rinse product downstream of the purification zone for recycle to the rotary pressure filter apparatus.

Additional features of the above-described processes for manufacturing and recovering purified forms of aromatic carboxylic acid in accordance with the present teachings will now be described in reference to the drawing figures.

FIG. 1 shows a process flow diagram for manufacturing and recovering purified forms of aromatic carboxylic acids in accordance with one embodiment of the present invention. As a brief introduction, the process 100 includes a reaction zone comprising an oxidation reactor 110 configured for liquid phase oxidation of feedstock; a crystallization zone configured for forming crude aromatic carboxylic acid from the liquid phase oxidation reaction mixture, and comprising crystallization vessels 152 and 156; a solid-liquid separation device 190 configured for separating crude aromatic carboxylic acid (and oxidation by-products) from liquid; a mixing zone including a purification reaction mixture make up vessel 200 configured for preparing mixtures of crude aromatic carboxylic acid in purification reaction solvent; a pre-heating zone including a pressurizing pump 206 and heat exchanger 208 for heating the purification reaction mixture prior to its introduction into a purification zone; a purification zone including a hydrogenation reactor 210 configured for contacting the crude aromatic carboxylic acid with hydrogen in the presence of a catalyst to form a purified aromatic carboxylic acid; a recovery zone comprising a crystallization zone 220 including at least one crystallization vessel configured for forming a slurry stream comprising solid purified aromatic carboxylic acid and a vapor stream, wherein the vapor stream comprises steam and hydrogen; a rotary pressure filter apparatus 230 configured for filtering the solid/liquid mixture to form a filter cake comprising the purified carboxylic acid solids; a dryer 235 for drying filter cake, and a separation zone 240 configured for receiving and flashing a pressurized wet gas stream from the rotary pressure filter apparatus 230 to form a gas stream 241 and a solid/liquid stream 242.

The integration of processes in FIG. 1 is meant to be purely representative, and various other integrated, and non-integrated configurations may likewise be used.

Liquid and gaseous streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams or compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

Representative aromatic feedstock materials suitable for use in the oxidation reactor 110 include but are not limited to aromatic compounds (e.g., hydrocarbons) substituted at one or more positions with at least one group that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as a hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). Representative feed compounds that may be used in accordance with the present teachings—alone or in combinations—include but are not limited to toluene; ethylbenzene and other alkyl-substituted benzenes; o-xylene; p-xylene; m-xylene; tolualdehydes, toluic acids, alkyl benzyl alcohols, 1-formyl-4-methylbenzene, 1-hydroxymethyl-4-methylbenzene; methylacetophenone; 1,2,4-trimethylbenzene; 1-formyl-2,4-dimethyl-benzene; 1,2,4,5-tetramethyl-benzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene, and the like); and the like; and partially oxidized derivatives of any of the foregoing; and combinations thereof. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Aromatic carboxylic acids manufactured in accordance with the present teachings are not restricted and include but are not limited to mono- and polycarboxylated species having one or more aromatic rings. In some embodiments, the aromatic carboxylic acids are manufactured by reaction of gaseous and liquid reactants in a liquid phase system. In some embodiments, the aromatic carboxylic acid comprises only one aromatic ring. In other embodiments, the aromatic carboxylic acid comprises a plurality (e.g., two or more) of aromatic rings that, in some embodiments, are fused (e.g., naphthalene, anthracene, etc.) and, in other embodiments, are not. In some embodiments, the aromatic carboxylic acid comprises only one carboxylic acid (e.g., —$CO_2H$) moiety or a salt thereof (e.g., —$CO_2X$, where X is a cationic species including but not limited to metal cations, ammonium ions, and the like). In other embodiments, the aromatic carboxylic acid comprises a plurality (e.g., two or more) of carboxylic acid moieties or salts thereof. Representative aromatic carboxylic acids include but are not limited to terephthalic acid, trimesic acid, trimellitic acid, phthalic acid, isophthalic acid, benzoic acid, naphthalene dicarboxylic acids, and the like, and combinations thereof. In some embodiments, the present teachings are directed to manufacture of pure forms of terephthalic acid including purified terephthalic acid (PTA) and so-called medium purity terephthalic acids.

A representative type of oxidation that may be conducted in the oxidation reactor 110 is a liquid phase oxidation that comprises contacting oxygen gas and a feed material comprising an aromatic hydrocarbon having substituents oxidizable to carboxylic acid groups in a liquid phase reaction mixture. In some embodiments, the liquid phase reaction mixture comprises a monocarboxylic acid solvent and water in the presence of a catalyst composition comprising at least one heavy metal component (e.g., Co, Mn, V, Mo, Cr, Fe, Ni, Zi, Ce, Hf, or the like, and combinations thereof) and a promoter (e.g., halogen compounds, etc.). In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in one or more reactors.

In a representative embodiment, such as may be implemented as shown in FIG. 1, liquid feed material comprising at least about 99 wt. % substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, and air may be continuously charged to oxidation reaction vessel 110 through inlets, such as inlet 112. In some embodiments, vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

In some embodiments, para-xylene is oxidized in reactor 110, predominantly to terephthalic acid. By-products that may form in addition to terephthalic acid include but are not limited to partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead gaseous stream that comprises vaporized acetic acid, water vapor, gaseous by-products from the oxidation reaction, carbon oxides, nitrogen from the air charged to the reaction, unreacted oxygen, and the like, and combinations thereof. In some embodiments the oxygen concentration in the gaseous effluent stream is measured directly upon leaving the reactor to ensure safe operation and product quality. In one embodiment, the oxygen analyzer system includes a high efficient condenser, a fast sample system, and a paramagnetic oxygen analyzer that are optimized to provide fast response time and efficient sample conditioning for improved quality control, reliability, and process safety. A triple redundant system is used to provide high reliability and process safety. The redundant analyzer system is used in a complex process control application to control the oxygen concentration of the oxidation reaction through an advanced air and feed mix process control application. The redundant oxygen analyzers are also used in the process safety application, the response time and trip limits are designed in tandem such that measurement lag is low enough to avoid passing into the flammable region before the analyzer can detect it.

In some embodiments, liquid effluent comprising solid oxidation products slurried in the liquid phase reaction mixture is removed from reaction vessel 110 through slurry outlet 114 and directed in stream 115 to crystallization vessel 152, and in turn crystallization vessel 156, for recovery of a solid product.

The gaseous stream may be removed from the reactor through vent 116 and sent in a stream 111 to a distillation column 160. The distillation column 160 is configured to separate water from the solvent monocarboxylic acid and return a solvent-rich liquid phase to the reactor in line 161. A distilled gaseous stream is removed from the distillation column 160 in line 164 for further processing. Reflux is returned to the distillation column 160 in line 165. The reflux fluid may include condensed portions of the water rich gas stream 164 or may include fluid from other sources, such as a liquid filtrate stream in stream 237. Examples of further processing of the overhead gas stream and sources of reflux fluids are more fully described in U.S. Pat. Nos. 5,723,656, 6,137,001, 7,935,844, 7,935,845, and 8,173,834.

In some embodiments, solid crude product may be recovered from the liquid by crystallization in one or more stages, such as in a single crystallization vessel or, as shown in FIG. 1, in a series of multiple stirred crystallization vessels. In some embodiments, the crystallization process comprises sequential reductions in temperature and pressure from earlier to later stages to increase product recovery. By way of example, as shown in FIG. 1, crystallization vessels 152 and 156 may be provided in series and in fluid communication, such that product slurry from vessel 152 may be transferred to vessel 156. Cooling in the crystallization vessels may be accomplished by pressure release. One or more of the crystallization vessels may be vented, as at vents 154 and 158, to remove vapor resulting from pressure let down and generation of steam from the flashed vapor to a heat exchange means (not shown).

As shown in FIG. 1, the crystallization vessel 156 is in fluid communication with a solid-liquid separation device 190. The solid-liquid separation device 190 is configured to receive a slurry of solid product from the crystallization vessel 156. In some embodiments, the solid-liquid separation device 190 is further configured to separate a crude solid product and by-products from the liquid. In some embodiments, the separation device 190 is a centrifuge, a rotary vacuum filter, a pressure filter, or the like, or a combination thereof. In some embodiments, the separation device 190 comprises a pressure filter configured for solvent exchange (e.g., by positive displacement under pressure of mother liquor in a filter cake with wash liquid comprising water). Suitable rotary pressure filters are sold by BHS-Sonthofen and are disclosed for example, in U.S. Pat. Nos. 2,741,369, 7,807,060, US Pat. App. 20050051473, US Pat. App. 20150182890, and WO2016014830. The oxidation mother liquor resulting from the separation may exit separation device 190 in stream 191 for transfer to mother liquor drum 192. A portion of the mother liquor and, in some embodiments, a major portion of the mother liquor, may be transferred from drum 192 to oxidation reactor 110. In such a way, monocarboxylic acid solvent, water, catalyst, and/or oxidation reaction by-products dissolved and/or present as fine solid particles in the mother liquor may be returned to the liquid phase oxidation reaction.

As shown in FIG. 1, the stream 197 comprising crude solid product may be directed to a mixing zone including a reaction mixture make up vessel 200. The crude solid product in stream 197 may be mixed and slurried in make-up vessel 200 with a make-up solvent entering vessel 200 through line 202 to form a purification reaction mixture comprising crude aromatic carboxylic acid. The purification reaction mixture prepared in vessel 200 is withdrawn through line 204. In some embodiments, the purification make-up solvent contains water. In some embodiments, the solvent line 202 connects to a holding vessel (not shown) for containing make-up solvent. In other embodiments, the solvent comprises fresh demineralized water fed from a deaerator. In other embodiments, the solvent is supplied from another part of the integrated process 100. For example, in one embodiment, the solvent comprises the condensate obtained from an off-gas separation in column 160 or from vapors recovered from a crystallization zone. In another embodiment, the solvent comprises the solid/liquid stream 242 exiting the separation zone 240. Sources of purification make-up solvent are more fully described, for example, in U.S. Pat. Nos. 5,723,656, 6,137,001, 7,935,844, 7,935,845, and 8,173,834.

Purification reaction mixture exiting vessel 200 through line 204 enters a pre-heating zone. The purification reaction mixture is introduced into the pre-heating zone at a pressure above ambient, which allows the purification reaction mixture to be introduced at a higher temperature than would have been possible if non-pressurized. The pre-heating zone shown in FIG. 1 includes a pump 206 and a heat exchanger 208. Those skilled in the art will appreciate that although only one heat exchanger is shown in FIG. 1, the pre-heating zone may include additional heat exchangers configured in series or parallel. The heat exchanger 208 raises the temperature of the purification reaction mixture to a temperature required for a purification reaction as described below. In one embodiment, the temperature is raised to at least 250° C. In one embodiment, the temperature is raised to about 290° C.

The heated purification reaction mixture exits the pre-heating zone and enters the purification zone. The purification zone includes a purification reactor 210. In some embodiments, the purification reactor 210 is a hydrogenation reactor and purification in the purification reactor 210 comprises contacting the purification reaction mixture comprising crude aromatic carboxylic acid with hydrogen in the presence of a hydrogenation catalyst. In some embodiments, at least a portion of the purification liquid reaction mixture may be continuously removed from hydrogenation reactor 210 in stream 211 and directed to a crystallization zone 220 downstream of the purification zone. Crystallization zone 220 may comprise a plurality of crystallizers (discussed below with reference to FIG. 4). In some embodiments, in crystallization zone 220, terephthalic acid and reduced levels of impurities may be crystallized from the reaction mixture. The resulting solid/liquid mixture comprising purified carboxylic acid solids formed in crystallization zone 220 may be fed to a rotary pressure filter apparatus 230 in stream 221.

In addition to the solid/liquid mixture in stream 221, a wash fluid and an inert gas are fed to the rotary pressure filter apparatus 230 in streams 231 and 232, respectively. In some embodiments, the inert gas may be nitrogen. In other embodiments, the inert gas may be a recycled process gas with about 95 percent nitrogen, some oxygen, and other impurities. The inert gas may dry a filter cake in the rotary pressure apparatus 230. In some embodiments, the wash fluid may be a deionized water stream. In other embodiments, the wash fluid may be a recycled water stream with some impurities. The wash fluid may remove impurities from the filter cake.

Figure 2:
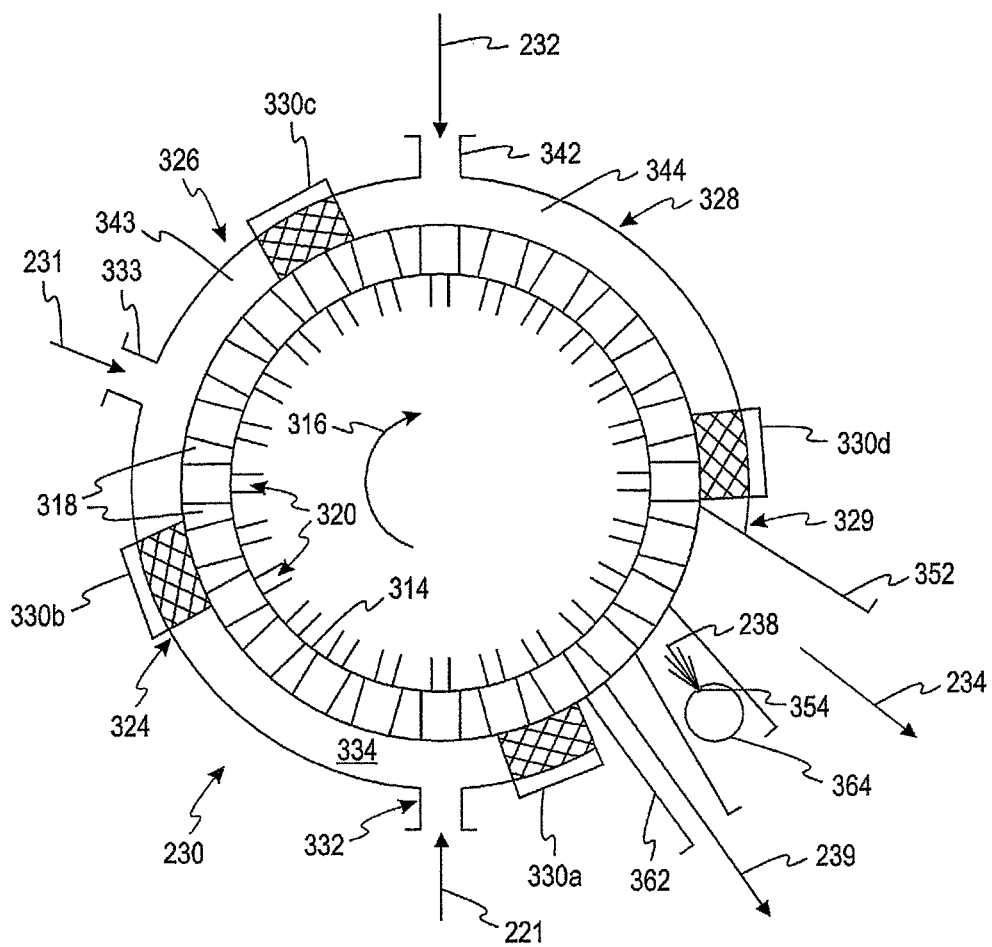
FIG. 2 shows a schematic drawing of a cross section of a rotary pressure apparatus in accordance with one embodiment of the present teachings.
Figure 3:
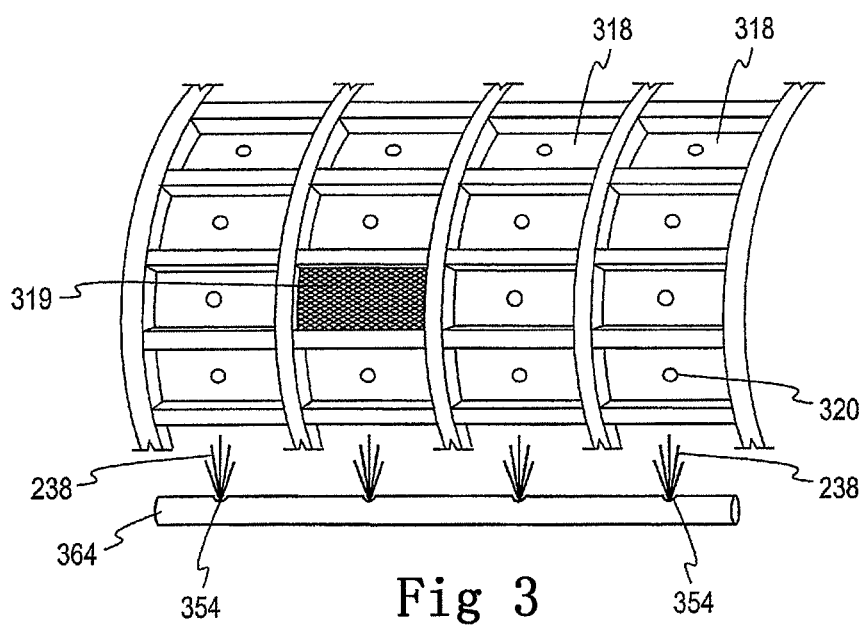
FIG. 3 shows an exploded perspective view of a portion of a rotary pressure filter apparatus with a filter rinse spray bar that is suitable for use in embodiments of the present teachings.

FIG. 2 illustrates one embodiment of a cross section of a rotary pressure filter apparatus 230. FIG. 3 illustrates an exploded perspective view of a portion of a rotary pressure filter apparatus 230. As shown in FIG. 2, the rotary pressure filter apparatus 230 comprises a rotating filter drum 314 which rotates as indicated by arrow 316. A plurality of compartments 318 are arranged around the circumference of the filter drum 314 and rotate with the filter drum 314. The compartments 318 each include a filter member 319 (shown in one compartment in FIG. 3) adjacent the filter drum 314. In some embodiments the filter member 319 comprises a filter cloth supported over a metal screen in a filter housing (not shown). In some embodiments, the filter cloth is manufactured from a polyether ether ketone (PEEK) polymer. Each compartment 318 also has associated with a corresponding outlet pipe 320 which also rotates with the filter drum 314 and the compartments 318. The outlet pipes 320 are configured such that filtrate from each compartment 316 passes through its corresponding filter member adjacent the filter drum 314 and into its corresponding outlet pipe.

The rotary pressure filter apparatus 230 also includes a number of stationary components. The rotary pressure filter apparatus 230 may be divided into a plurality of zones, including a filtering zone generally shown at 324, a wash zone generally shown at 326, a drying zone generally at 328 shown a discharge zone generally shown at 329. The filtering zone 324 defines the first stage of a multi-stage process for separating and recovering a solid product from solid-liquid mixtures. Each of the zones are separated from the adjacent zones by sealing members 330a, 330b, 330c, and 330d.

The solid-liquid mixture stream 221 enters the filtering zone 324 of the rotary pressure filter apparatus 230 through inlet 332. The inlet 332 is in fluid communication with plenum 334 which distributes the solid-liquid mixture into compartments 318. As a result of the pressure differential that is maintained between the compartments 318 and the outlet pipes 320 and across the filter member in the compartments, liquid filtrate of the solid-liquid mixture is forced through the filter member in the compartments 318 and into outlet pipes 320. The outlet pipes 320 are in fluid communication with filtrate discharge pipes (not shown) for removing the liquid filtrate 237 from the rotary pressure apparatus 230. The solid components of the solid-liquid mixture remain on the filter member in the form a filter cake.

The compartments 318 now having filter cake continue their rotation into wash zone 326. A wash fluid stream 231 is introduced into the wash zone 326 through inlet 333. The inlet 333 is in fluid communication with plenum 343 which distributes the wash fluid into compartments 318. As a result of the pressure differential that is maintained between the compartments 318 and the outlet pipes 320 and across the filter member in the compartments, the wash fluid is forced into the filter cake that resides on the filter member in the compartments 318 to form a wet filter cake. A portion of the wash fluid is removed through the filter member and into the outlet 320 (as liquid filtrate), taking with it impurities and residual liquids from the solid-liquid mixture that may have adhered to the filter cake or residing in voids of the filter cake. Another portion of the wash fluid remains with the now wet filter cake.

The compartments 318 now having wet filter cake continue their rotation into drying zone 328, where an inert drying gas is introduced into the drying zone 328 through inlet 342. The inlet 342 is in fluid communication with plenum 344 which distributes the inert gas into compartments 318. Drying zone 328 may displace the liquid in the wet filter cake down to about 8-15 weight percent forming a dried filter cake and a wet gas stream. The wet gas stream exits the rotary pressure apparatus 230 through outlet pipes 320 in the drying zone 328. The outlet pipes 320 are in fluid communication with a wet gas line 233 (shown in FIG. 1) for removing the wet gas stream from the rotary pressure apparatus 230.

The compartments 318 now having dried filter cake continue their rotation into discharge zone 329. The dried filter cake may be discharged by gravity through discharge outlet 352 as stream 234. In some embodiments, the discharge zone 329 includes a filter cake disengaging device (not shown), such as a blower or scraper to assist with the discharge of the wet filter cake. The filter cake 234 may be dried in a dryer 235, such as a rotary steam tube dryer, to form a purified aromatic carboxylic acid product. The dryer 235 may dry the filter cake until less than about 0.2 weight percent liquid remains in the purified carboxylic acid product. The purified aromatic carboxylic acid product may exit the dryer 235 through stream 236

The wet gas stream exits the drying zone 328 of the rotary pressure filter apparatus 230 through outlet pipes 320 and proceeds through wet gas line 233 to separation zone 240. The liquid filtrate stream exits the filtering zone 324 and, in some embodiments, the wash zone 326 of the rotary pressure filter apparatus 230 through outlet pipes 320 to form stream 237. The liquid filtrate stream in stream 237 may be returned to the distillation column 160 in line 165. The liquid filtrate stream may comprise water, acetic acid, and dissolved solids (organic acids).

The purified aromatic carboxylic acid solids remaining on the filter members 319 is typically removed by steps of rinsing the filter members 319 from the exterior side (i.e., the side facing the outside of the rotary pressure apparatus 230), producing a "filter rinse product" comprising the purified aromatic carboxylic acid. The filter rinse solution may be injected into the rotary pressure filter apparatus 230 with a filter rinse spray bar 364 which extends the length of the rotary pressure filter drum 314 (see FIG. 3). The filter rinse solution enters the filter rinse spray bar 364 at one of the ends and exits nozzles 354 in stream(s) 238 in order to wash the filter members of the compartments 318 before they continue into the next cycle through the rotary pressure filter apparatus 230. In one embodiment, the filter rinse solution may exit the nozzles 354 in a conical spray pattern. After rinsing, the filter rinse product exits the rotary pressure filter apparatus 230 via gravity through filter rinse drain 362 to form filter rinse product stream 239.

In one embodiment, the wash solution may be water. The water for washing the filter cloth may be at a temperature of between about 90 degrees Celsius and about 150 degrees Celsius, preferably between about 95 degrees Celsius and about 110 degrees Celsius.

Those skilled in the art will appreciate that other configurations of the rotary pressure filter apparatus 230 may be used in accordance with the present invention.

At least a portion of the filter rinse product 239 is directed to a point in the process that is downstream of the purification zone but upstream of the rotary pressure filter apparatus 230 so that it may be recycled to the rotary pressure filter apparatus 230. By directing the filter rinse product 239 to a point in the process downstream of the purification zone, the filter rinse product 239 does not have to be pre-heated or dissolved for the purification reaction in reactor 210, and therefore energy is saved. In the embodiment shown in in FIG. 4, a recycling line 402 may direct the filter rinse product in stream 239 to a crystallization zone 220. In alternate embodiments, the filter rinse product 239 may be directed to other points in the process which are downstream of the purification zone but upstream or downstream of the crystallization zone 220. In one embodiment, the filter rinse product is not substantially redissolved prior to entering the crystallization zone 220. Thus, the filter rinse product does not need to be heated and may be at a temperature of below about 150 degrees Celsius, in some embodiments at a temperature of about 100 degrees Celsius. Below 150 degrees Celsius, less than 5 percent of the solids in the filter rinse products are redissolved. In some embodiments, less than 3 percent of the solids in the filter rinse product are redissolved. In other embodiments, less than 1 percent of the solids in the filter rinse product are redissolved. Eliminating heating of the filter rinse product reduces the amount of energy needed to run the process.

The recycling line 402 may direct the filter rinse product 239 to a drum 404. The filter rinse product may be pumped from the drum 404 with a pump 405 to the crystallization zone 220. The stream entering the crystallization zone 220 needs to be at a pressure of between about atmospheric pressure and about 8 bar, preferably between about 3 bar and about 7 bar, most preferably between about 4 bar and about 6 bar. Pump 405 may be used to increase the pressure of the filter rinse product in recycling line 402, which is at about atmospheric pressure after leaving the rotary pressure filter apparatus 230. During the continuous process, the drum 404 may be used to temporarily hold a volume of filter rinse product to allow the pump 405 to increase the pressure of the filter rinse product in the recycling line 402 prior to directing it to the crystallization zone 220. In other embodiments, the filter rinse product may be directed to the crystallization zone 220 without increasing the pressure (i.e., at atmospheric pressure).

In some embodiments, the filter rinse product may be heated in a heat exchanger 406 prior to being directed to the crystallization zone 220. The heat exchanger 406 may heat the filter rinse product to up to 150 degrees Celsius in order to dissolve fines (small particles of solid purified carboxylic acid product that are difficult to filter). The reduced amount of fines may also prevent build up on filters throughout the process. Even utilizing the heat exchanger 406, however, less than 10 percent of the solids are substantially redissolved.

Figure 4:
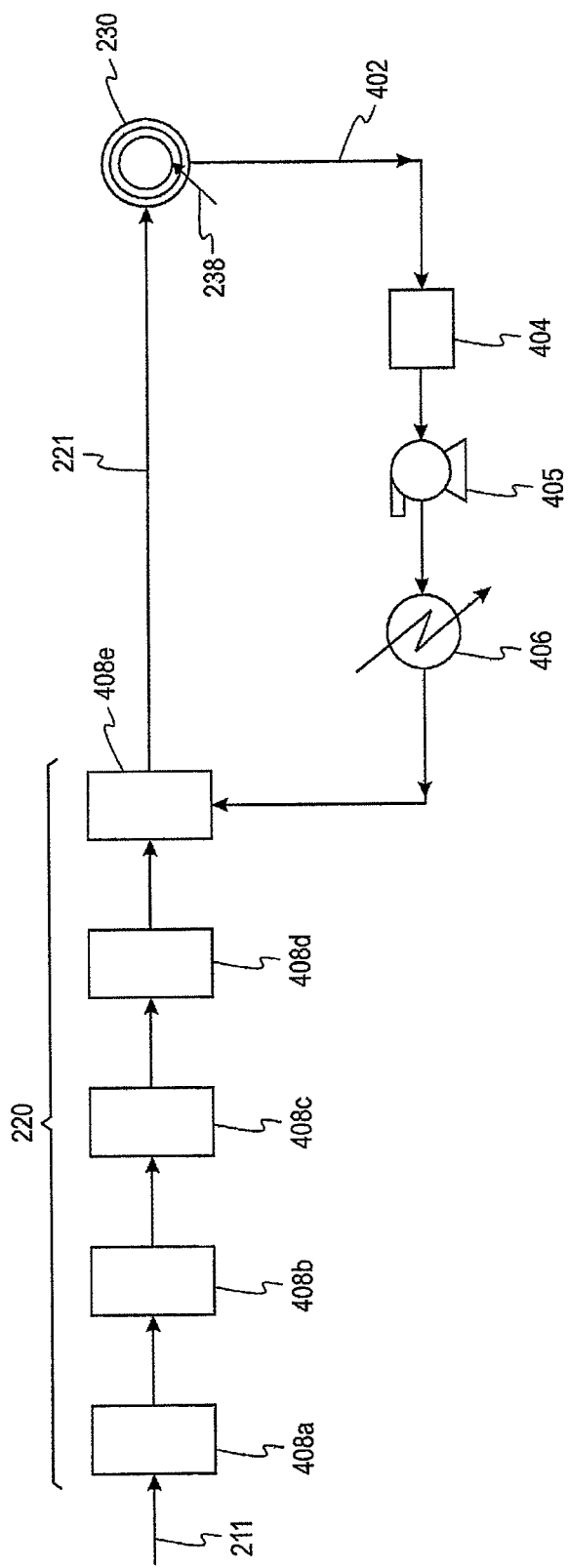
FIG. 4 shows a portion of a process flow diagram for manufacturing and recovering purified forms of aromatic carboxylic acids in accordance with one embodiment of the present teachings.

As shown in FIG. 4, the crystallization zone 220 may comprise a plurality of crystallizers 408a, 408b, 408c, 408d, and 408e in series. In one embodiment, the filter rinse product 239 may be directed to the last crystallizer 408e in the sequence. By directing the filter rinse product to the last crystallizer in the sequence, unnecessary throughput of the other crystallizers is avoided.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for manufacturing a purified aromatic carboxylic acid comprising:
   purifying a crude aromatic carboxylic acid in a purification zone to form a purified aromatic carboxylic acid;
   crystallizing a purified aromatic carboxylic acid in a crystallization zone to form a solid/liquid mixture comprising purified aromatic carboxylic acid solids, wherein the crystallization zone comprises a plurality of crystallizers in series;
   filtering the solid/liquid mixture through a filter member of a rotary pressure filter apparatus to form a filter cake comprising the purified aromatic carboxylic acid solids;
   removing the filter cake from the filter member;
   rinsing the filter member to produce a filter rinse product, wherein the filter rinse product comprises purified aromatic carboxylic acid; and
   directing at least a portion of the filter rinse product downstream of the purification zone for recycle to the rotary pressure filter apparatus, said recycle being via a recycling line and a pump that increases the pressure of the filter rinse product in the recycling line.

2. The process of claim 1, further comprising recovering the purified aromatic carboxylic acid solids from the filter cake.

3. The process of claim 1, wherein directing at least a portion of the filter rinse product downstream of the purification zone comprises directing at least a portion of the filter rinse product to the crystallization zone.

4. The process of claim 1, wherein the filter rinse product is not substantially redissolved prior to recycle to the rotary pressure filter apparatus.

5. The process of claim 4, wherein less than 5 percent of the filter rinse product is redissolved.

6. The process of claim 1, further comprising heating the filter rinse product in order to dissolve fines in the filter rinse product.

7. The process of claim 1, wherein directing at least a portion of the filter rinse product downstream of the purification zone comprises directing at least a portion of the filter rinse product to a drum and pumping with the pump the filter rinse product from the drum.

8. The process of claim 1, further comprising oxidizing a substituted aromatic compound in an oxidation reactor to form the crude aromatic carboxylic acid.

9. The process of claim 1, wherein the purifying a crude aromatic carboxylic acid in a purification zone comprises contacting a crude aromatic carboxylic acid with hydrogen in the presence of a catalyst in a hydrogenation reactor to form at least a portion of the purified aromatic carboxylic acid fed to the crystallization zone.

10. The process of claim 1, further comprising drying the filter cake to form a purified carboxylic acid product.

11. The process of claim 1, wherein the filter rinse product is directed to a last crystallizer in the sequence.

12. The process of claim 1, wherein the aromatic carboxylic acid comprises terephthalic acid.

13. The process of claim 1, wherein the filter member is a filter cloth.

14. The process of claim 13, wherein the filter cloth comprises polyether ether ketone polymer.

* * * * *